United States Patent
Cameron et al.

(10) Patent No.: US 6,796,429 B2
(45) Date of Patent: Sep. 28, 2004

(54) TRANSDERMAL/TRANSMUCOSAL PATCH PACKAGING

(75) Inventors: Brian D. Cameron, Stillwater, MN (US); Shu Kun Chang, Chicago, IL (US); Stacey H. Chang, Sunnyvale, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 204 days.

(21) Appl. No.: 10/244,241

(22) Filed: Sep. 16, 2002

(65) Prior Publication Data

US 2003/0075470 A1 Apr. 24, 2003

Related U.S. Application Data

(60) Provisional application No. 60/339,537, filed on Oct. 22, 2001.

(51) Int. Cl.[7] ................................................ B65D 85/52
(52) U.S. Cl. ......................................... 206/440; 206/804
(58) Field of Search ............................. 53/443, 450, 452, 53/461, 467; 206/438, 440, 804, 812, 494

(56) References Cited

U.S. PATENT DOCUMENTS

| | | | |
|---|---|---|---|
| 3,918,608 A | | 11/1975 | Faller |
| 3,979,020 A | | 9/1976 | Braber et al. |
| 4,963,360 A | * | 10/1990 | Argaud ........................ 424/443 |
| 5,698,217 A | * | 12/1997 | Wilking ....................... 424/448 |
| 5,816,441 A | | 10/1998 | Farside |
| 5,950,830 A | * | 9/1999 | Trigger ........................ 206/440 |
| 6,168,028 B1 | * | 1/2001 | Telesca et al. .............. 206/776 |

FOREIGN PATENT DOCUMENTS

| | | |
|---|---|---|
| EP | 0 930 243 | 7/1999 |
| WO | WO 98/24393 | 6/1999 |

* cited by examiner

Primary Examiner—Jacob K. Ackun, Jr.
(74) Attorney, Agent, or Firm—Ted Ringsred; Robert Sprague

(57) ABSTRACT

A dispenser for conveniently dispensing multiple transdermal/transmucosal drug-containing patches from a single container. The dispenser has an inner cartridge defined by walls made of an impermeable material, wherein the inner cartridge is hermetically sealed during storage. In another aspect, the dispenser incorporates a child-resistant mechanism.

26 Claims, 6 Drawing Sheets

TRANSDERMAL/TRANSMUCOSAL PATCH PACKAGING

This application claims the benefit of provisional application Ser. No. 60/339,537, filed Oct. 22, 2001.

The present invention relates to packaging for transdermal/transmucosal drug delivery patches.

BACKGROUND OF THE INVENTION

Transdermal and transmucosal patches containing drugs such as estradiol, levonorgestrel, testosterone, scopolamine, nitroglycerin, nicotine, heparin, melatonin, diagnostic compounds, and other ingredients are conventionally required to be packaged in hermetically sealed, individual foil and/or plastic pouches. Such packaging is necessary in order to maintain sanitary conditions and to prevent degradation, contamination, and/or loss of sensitive ingredients by environmental exposure. In many cases, the material used for such packaging has to be sufficiently impervious to volatile active ingredients, e.g., nitroglycerin, and environmental factors, e.g., humidity, to allow the device to remain stable under extended storage conditions of up to several years.

A serious disadvantage of conventional packaging is that the user must tear open a separate pouch each time one of the transdermal or transmucosal patches is needed. Furthermore, it is desirable for many pharmaceutical products that the packaging material be difficult to open by children, so called "child-resistant" packaging. These conventional pouches may not be child-resistant, but can be difficult to open, particularly for the elderly and those with conditions that impair strength and/or manual dexterity, and especially if the packaging is made of tear resistant or hard to grasp materials. Even for those without any special difficulties, opening such pouches on a frequent basis over an extended period can be a substantial inconvenience. Moreover, individual packaging can be expensive and wasteful due to the excessive packaging material required and manufacturing cost for individual packaging.

It would be desirable to package transdermal and transmucosal drug-containing patches so as to be simple to open for adult patients, difficult for children to open, economical, sufficiently impervious to prevent loss of volatile components, and easy to manufacture.

SUMMARY OF THE INVENTION

The present invention provides a dispenser for conveniently dispensing multiple transdermal/transmucosal drug-containing patches from a single container. The dispenser has a separate inner cartridge having walls made of an impermeable material, wherein the inner cartridge is hermetically sealed during storage. A plurality of individual patches are contained within the inner cartridge, and the patches can be removed from the dispenser through at least one aperture. The dispenser further comprises a housing comprising a base and an exterior cover, wherein the housing is adapted to fully enclose the inner cartridge and is capable of forming an impermeable seal defining an outer chamber.

In one preferred embodiment, the aperture of the inner cartridge is sealed with a foil seal, such that the inner cartridge is hermetically sealed during storage. The seal is then opened, broken, or otherwise removed in order to allow the enclosed transdermal patches to be removed from the inner cartridge during use. The inner cartridge is enclosed by a housing having a base and an exterior cover.

Preferably, the aperture has a secondary seal, such as a plastic film with a slit in the middle, or overlapping plastic films, which allows the patches to be removed, but otherwise minimizes air transfer into the inner cartridge and serves as a barrier for foreign debris.

In use, the inner cartridge is contained within the housing that contains other functional portions of the dispenser, such as a cover, buttons or other opening mechanisms, as well as defining the cosmetic appearance of the dispenser.

One benefit of this embodiment is the ability to improve stability, since the inner cartridge is the primary stability container closure during shelf life. The housing only has to maintain stability of the transdermal patch from the time that the inner cartridge seal is removed until the transdermal patches are exhausted from the dispenser. Separation of the inner cartridge and housing functions allows greater design flexibility for the housing, since cosmetic changes can be made to the housing with little or no impact on the pharmaceutical stability. Separation of the inner cartridge and housing functionality also provides the ability to make manufacturing processes more efficient and low cost, as well as providing for more convenient means of allowing the dispenser to be refillable.

In another aspect, the present invention provides a cartridge for use in a transdermal/transmucosal patch dispenser. The inner cartridge has walls made of an impermeable material, wherein the inner cartridge is hermetically sealed during storage. A plurality of individual patches is contained within the inner cartridge, and the patches can be removed from the cartridge through at least one aperture. The cartridge is adapted to be enclosed by a housing comprising a base and an exterior cover, wherein the housing is capable of forming an impermeable seal defining an outer chamber.

In yet another aspect, the present invention provides a dispenser for conveniently dispensing multiple transdermal/transmucosal drug-containing patches from a single container, wherein a child-resistant mechanism is incorporated into the dispenser. The dispenser has an inner cartridge defined by walls made of an impermeable material, wherein the inner cartridge is hermetically sealed during storage. A plurality of individual patches is contained within the inner cartridge, and the patches can be removed from the dispenser through at least one aperture. The dispenser further comprises an exterior cover adapted to enclose the aperture when the exterior cover is in a closed position.

The child-resistant mechanism can consist of a locking mechanism, a "lock-out" mechanism, an opening mechanism not readily apparent to children or not readily engaged by children, or any combination of the above. Locking mechanisms may include, for example, keypad or combination locks, keyed locks, or locks activated by biometric identification, such as through use of fingerprints. A "lock-out" mechanism may, for example, need to be activated by a magnetic or radio frequency identification signal before allowing the mechanism to open. Preferably, one or more triggering mechanisms, such as buttons, latches, levers, and the like, would have to be appropriately engaged before the dispenser could be opened for dispensing medicine. A "gravity switch" (i.e., a switch, latch, lock, or similar mechanism having gravity dependent operability related to physical orientation) could be employed, wherein engagement of the triggering mechanism allows the dispenser to open only if the dispenser is held in a particular, fixed orientation, such as parallel to the ground. Placing the dispenser in the proper alignment with relation to the ground, such that the gravity switch allows the dispenser to open, can be described as "engaging" the gravity switch.

In a particularly preferred embodiment, the dispenser is opened by activating a button while the dispenser is aligned such that a gravity switch is engaged.

In another particularly preferred embodiment, the dispenser is opened by simultaneously activating two (or more)

buttons while the dispenser is aligned such that the gravity switch is engaged.

One benefit of this invention is to reduce the likelihood of a non-user being accidentally exposed to the active pharmaceutical ingredients in a transdermal/transmucosal patch. Additionally, embodiments with locking mechanisms can be used to deter abuse of the transdermal patches and "lockout" mechanisms can be used to prevent patients from dosing with too many patches at one time. In a preferred embodiment, the dispenser has a lock-out mechanism and contains a controlled substance (e.g., a substance regulated in the United States by the Drug Enforcement agency), such as morphine, fentanyl, buprenorphine, or testosterone.

The transdermal/transmucosal patches are preferably arranged such that the removal of one patch thereby allows the next patch to be grasped and removed, and more preferably the patches are separably interconnected together such that the action of removing one of the transdermal/transmucosal patches thereby moves another patch into position for subsequent removal.

In a particularly preferred embodiment, the dispenser walls defining the inner cartridge are made of rigid plastic and the aperture is in the form of a single slot through which each of the transdermal/transmucosal patches is pulled. Each patch is preferably separably interconnected to an adjacent patch so that pulling one patch out of the slot pulls a portion of the next patch through the slot and into position for subsequent grasping and removal. The separable interconnection of the patches is preferably accomplished in one of essentially three ways:

(1) via a continuous release liner upon which the individual transdermal/transmucosal patches are commonly adhered, in which case the liner is preferably perforated between each patch to facilitate separation, (2) without a continuous release liner, but where there is either an added portion of adhesive between the release liner and backing of successive patches or where a part of the adhesive underside of one patch is directly adhered to a portion of the top surface of the next patch to be dispensed, or (3) without a continuous release liner, but where a portion of each patch is interleaved beneath a portion of the next patch to be dispensed.

The patches, which generally are not individually packaged, may be folded, stacked, and/or interleaved together one on top of another within the cartridge so that a large number of patches can be stored efficiently in a small space.

Alternatively, the individual transdermal/transmucosal patches may not be folded, stacked, and/or interleaved on top of each other, but instead arranged sequentially on a roll, or on a flat strip or continuous loop arrangement. In this case, depending on the design, the dispenser may have either a single aperture or multiple apertures (one for each patch). Also, the aperture may include a resilient sealing member to help prevent escape of volatile components and/or environmental contamination of the transdermal/transmucosal patch-containing cartridge.

Moreover, the dispenser may contain additional features, such as a desiccant, a moisture exposure indicator strip, a ratcheting mechanism, or a counter mechanism as described in copending U.S. patent application Ser. No. 08/982,813 (Richard G. Sitz et al.), the disclosure of which is incorporated herein by reference.

Preferred drug-containing transdermal/transmucosal patches to be dispensed from a dispenser according to the present invention are those which are administered on a weekly, twice-weekly, or daily basis, such as hormone replacement therapy and fertility control patches containing, for example, estradiol, progestins, and/or testosterone. Other examples of preferred patches include frequently applied patches such as nitroglycerin, nicotine, and fentanyl.

Finally, the present invention also provides a method of packaging transdermal/transmucosal drug-containing patches for convenient dispensing, comprising the steps of (i) providing a dispenser unit having walls defining an inner cartridge, an aperture, and a housing adapted to fully enclose the inner cartridge, and (ii) packaging a plurality of transdermal/transmucosal drug-containing patches within the inner cartridge and, preferably, arranging the patches so as to allow (and preferably require) removal of one patch at a time in a predetermined sequential order through the aperture.

BRIEF DESCRIPTION OF THE DRAWINGS

Preferred embodiments of the invention will now be described in greater detail below with reference to the attached drawings, wherein.

DETAILED DESCRIPTION OF THE INVENTION

Figure 1:
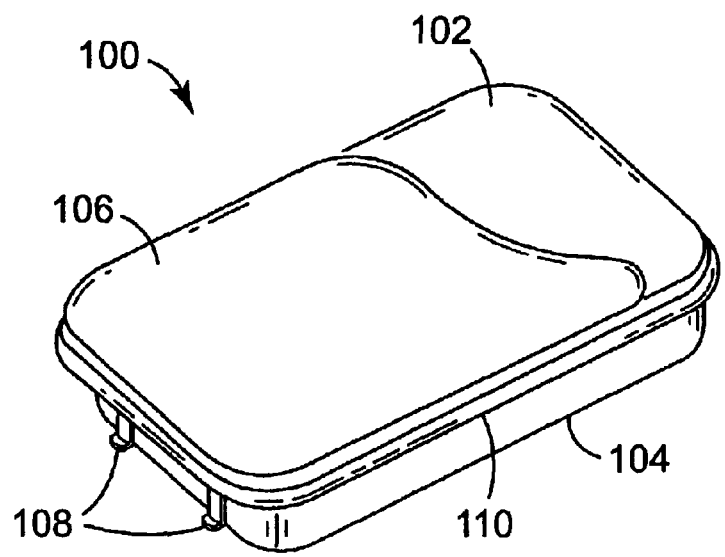
FIG. 1 is a perspective view of the inner cartridge.

FIG. 1 shows the inner cartridge 100 of a dispenser according to a preferred embodiment of the invention. The inner cartridge 100 includes an inner cartridge top 102, an inner cartridge bottom 104, and optional attachment tabs 108. In this figure the inner cartridge is sealed with a foil seal 106 that covers the inner aperture 112 (shown in FIG. 2). An optional gasket 110 may be included to allow an impermeable seal to be created between the housing 200 (shown in FIG. 3) and the inner cartridge top 100.

The foil seal 106 is preferably made such that it is sufficiently impermeable to prevent substantial losses of volatile components of the transdermal/transmucosal patches and/or degradation or contamination from environmental factors, such as humidity, microbes, and the like.

Figure 2:
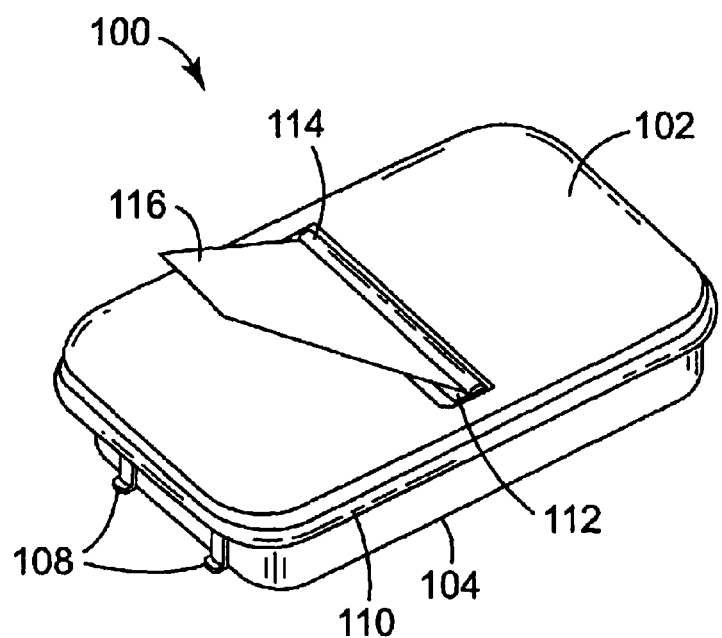
FIG. 2 is a perspective view of the inner cartridge after the aperture seal has been removed.

As shown in FIG. 2 a portion of the transdermal/transmucosal drug-containing patch 116 extends through inner aperture 112. The transdermal/transmucosal patch 116 has been shown, for convenience, as a single film layer. It will be understood that the transdermal/transmucosal patch will typically be composed of two or more layers, including a backing layer and at least one adhesive layer. The transdermal/transmucosal patch may also comprise a release liner that is removed before use. The drug in the transdermal/transmucosal patches may be in a reservoir or mixed into at least one of the layers of the adhesive or backing layers. Excipients, such as penetration enhancers and crystallization inhibitors, may also be included. Also, it should be noted that there is no requirement that the transdermal/transmucosal patches be uniform, layered transdermal/transmucosal patches such as those shown. For example, the patches may vary in size or shape and may include various structures, such as drug reservoirs.

When grasped and pulled by a user, the transdermal/transmucosal drug-containing patch 116 can be removed from the dispenser and a next transdermal/transmucosal patch will be concurrently pulled into place with a portion thereof extending out through the inner aperture 112.

Suitable materials for use as the inner cartridge 100 include, for example, polyetherimide; polyethylene, such as high density polyethylene and low density polyethylene; polypropylene; polypropylene copolymers with other olefins; polycarbonate; polymethylmethacrylate; polyamides; styrene-acrylonitrile (SAN) polymers; acrylonitrile-styrene-butadiene (ABS) polymers; and polyesters, such as polybutylene terephthalate and polyethylene terephthalate. It should be understood that the cartridge is sufficiently impermeable to prevent substantial losses of volatile components of the transdermal/transmucosal patches and/or prevent degradation or contamination from environmental factors, such as humidity, microbes, and the like. One skilled in the art will appreciate that the types of material that are sufficiently impermeable may vary depending upon the nature and chemical constituents of the transdermal/transmucosal patches contained within the cartridge.

Figure 3:
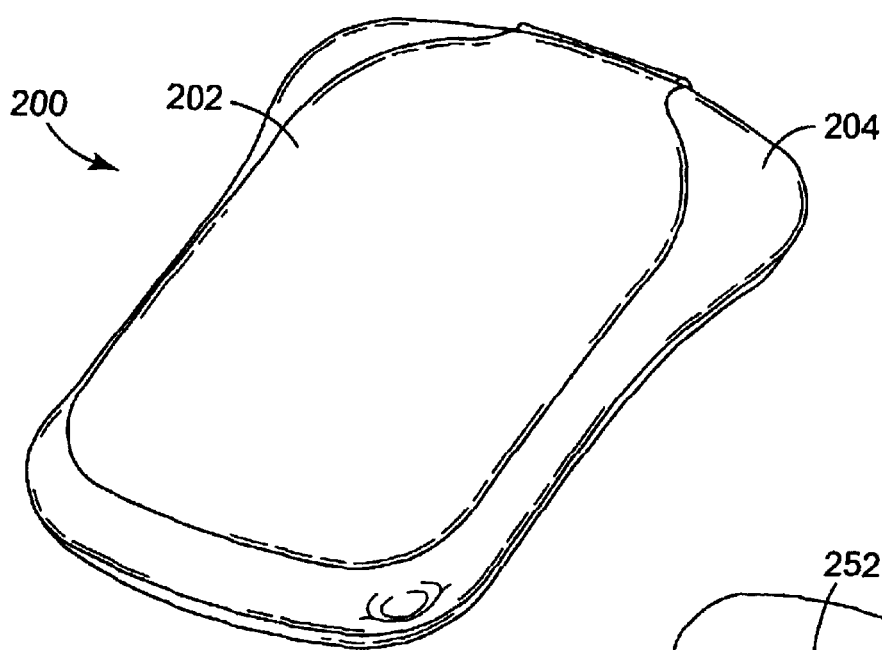
FIG. 3 is a perspective view of the housing in the closed position.
Figure 4:
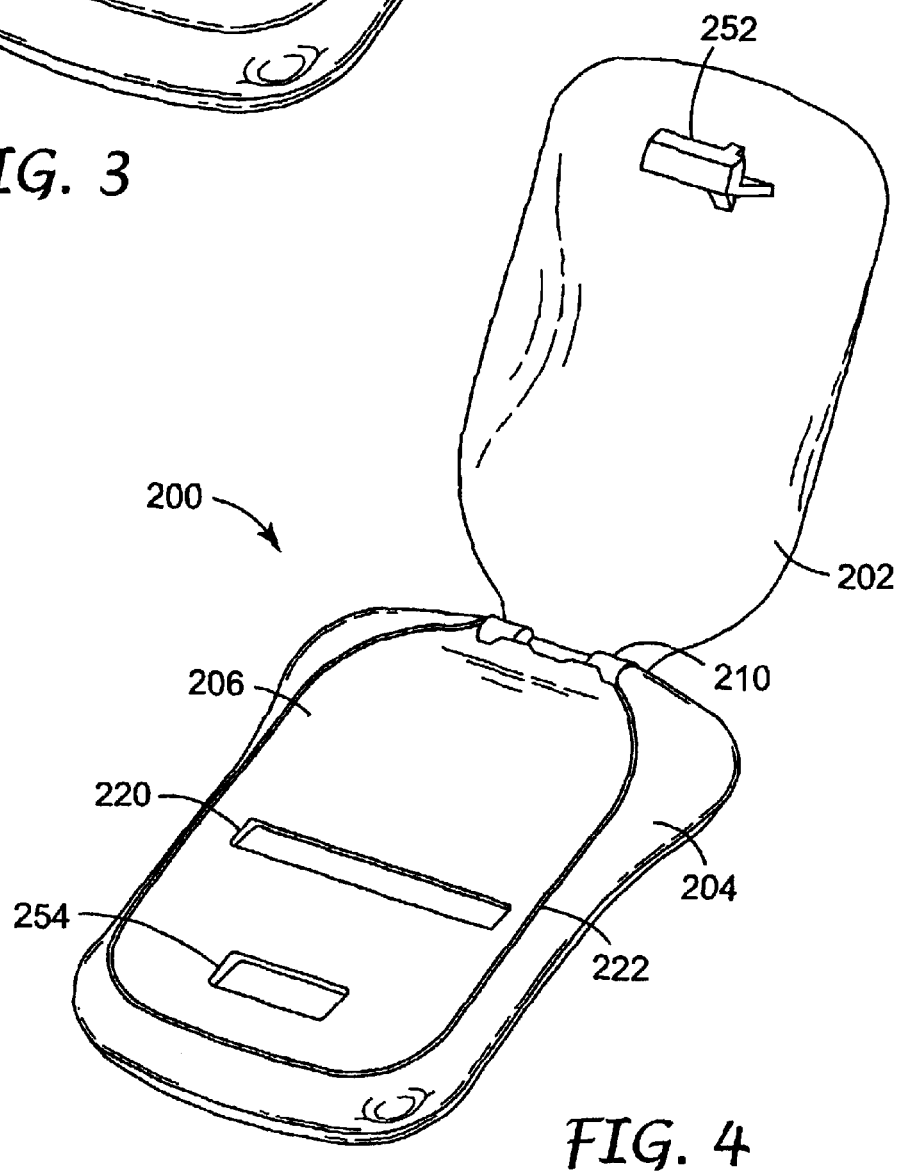
FIG. 4 is a perspective view of the open position of an embodiment of the housing with a base face plate.

The inner cartridge 100 shown in FIGS. 1 and 2 is placed within a housing 200 shown in FIG. 3 wherein the exterior cover 202 is in a closed position against the base 204. The attachment tabs 108 (shown in FIGS. 1 and 2) may facilitate joining of the inner cartridge 100 to the housing 200. The exterior cover may be secured in the closed position with a latch hook 252 that engages a latch slot 254 (shown in FIG. 4). FIG. 4 shows the housing 200 in the open position, where the exterior cover 202 has been rotated to the open position along the hinge 210 revealing the base face plate 206, which makes up the upper surface of the base. The base face plate aperture 220 is situated in relation to the inner aperture 112 so that the transdermal/transmucosal drug-containing patch 116 that extends from the inner aperture 112 will also extend through the base face plate aperture 220. In this embodiment, the foil seal 106 will also have a tab extending through the base face plate aperture 220 which allows the foil seal to be removed prior to initial use. The exterior cover 202 forms a seal with the base face plate 206 to provide sealing of the dispenser after the foil seal 106 has been removed. In a preferred embodiment, a gasket 222 may be used to enhance the seal between the exterior cover 202 and the base face plate 206.

Suitable materials for use as the gasket 222 include, for example, fluorocarbon polymers, ethylene propylene (EP) rubber, ethylene propylene diene (EPDM) rubber, styrenic block copolymers, nitrile rubber, and butyl rubber.

Suitable materials for use as the housing 200 include, for example, polyethylene, such as high density polyethylene and low density polyethylene; ethylene copolymers with other olefins, such as linear low density polyethylene or ultra low density polyethylene; polypropylene; polypropylene copolymers with other olefins; polycarbonate; polymethylmethacrylate; polyamides; styrene-acrylonitrile (SAN) polymers; acrylonitrile-styrene-butadiene (ABS) polymers; and polyesters, such as polybutylene terephthalate and polyethylene terephthalate. It should also be understood that the housing may consist of any polymers or copolymers suitable for use in injection molding, blow molding, or extrusion processing.

Figure 5:
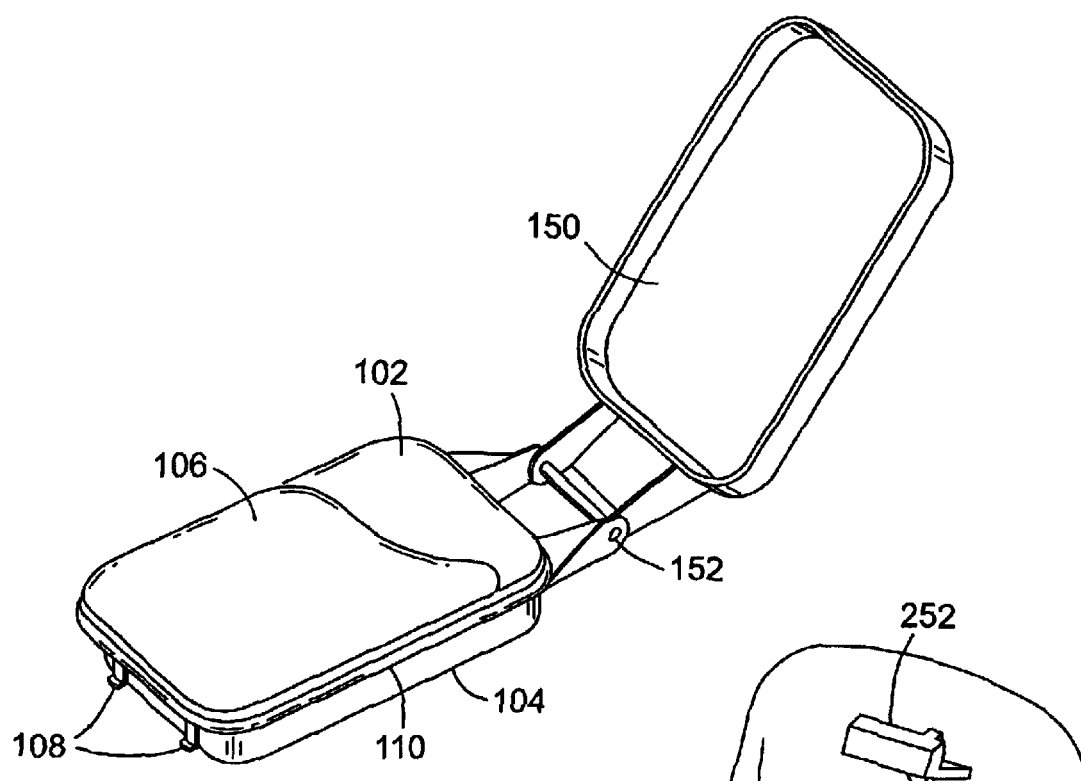
FIG. 5 is a perspective view of the inner cartridge with an interior cover in the open position.
Figure 6:
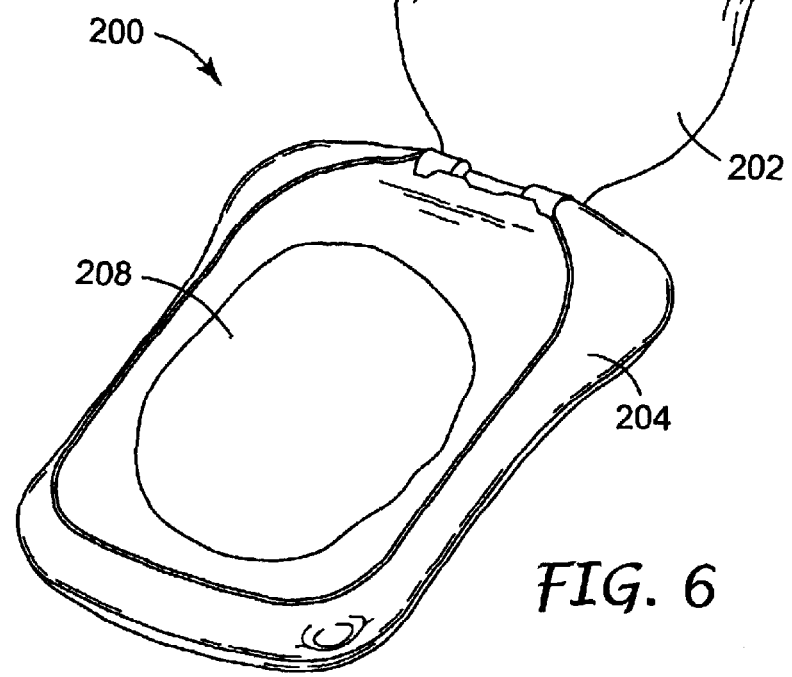
FIG. 6 is a perspective view of another embodiment of a housing in the open position.

In another embodiment, shown in FIG. 5, an interior cover 150 may be attached to the inner cartridge bottom 104 via a hinge 152. In this embodiment the base 204 of the housing 200 contains an open cavity 208 (shown in FIG. 6) where the inner cartridge is placed. The interior cover 150 is attached to the exterior cover 202, such that the interior cover 150 is a part of the housing and will open in conjunction with opening of the exterior cover 202. This attachment is preferably by welding or fusing of the outer surface of the interior cover 150 to the inner surface of the exterior cover 202. Opening of the interior cover 150 reveals the inner cartridge top 102. The interior cover 150 forms a seal with the inner cartridge top 102. In a preferred embodiment, a gasket 110 may be used to enhance the seal between the interior cover 150 and the inner cartridge top 102. In this embodiment, stability after removal of the foil seal 106 is provided entirely by the inner cartridge 100, gasket 110, and interior cover 150. The external portions of the housing 200 do not need to provide stability and may be designed entirely to meet cosmetic or other use requirements.

Figure 7:
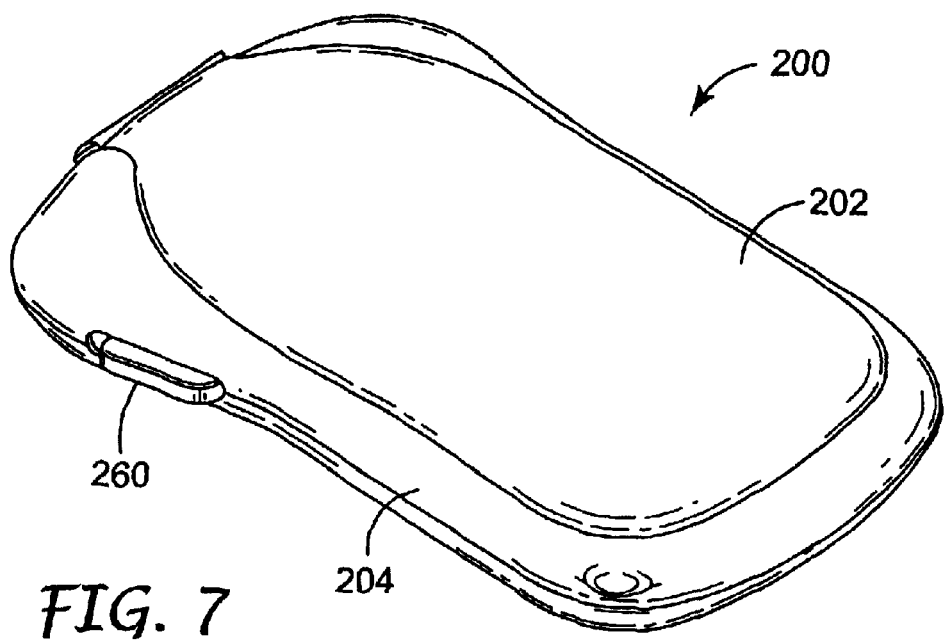
FIG. 7 is a perspective view of the closed position of a housing with a side button.
Figure 8:
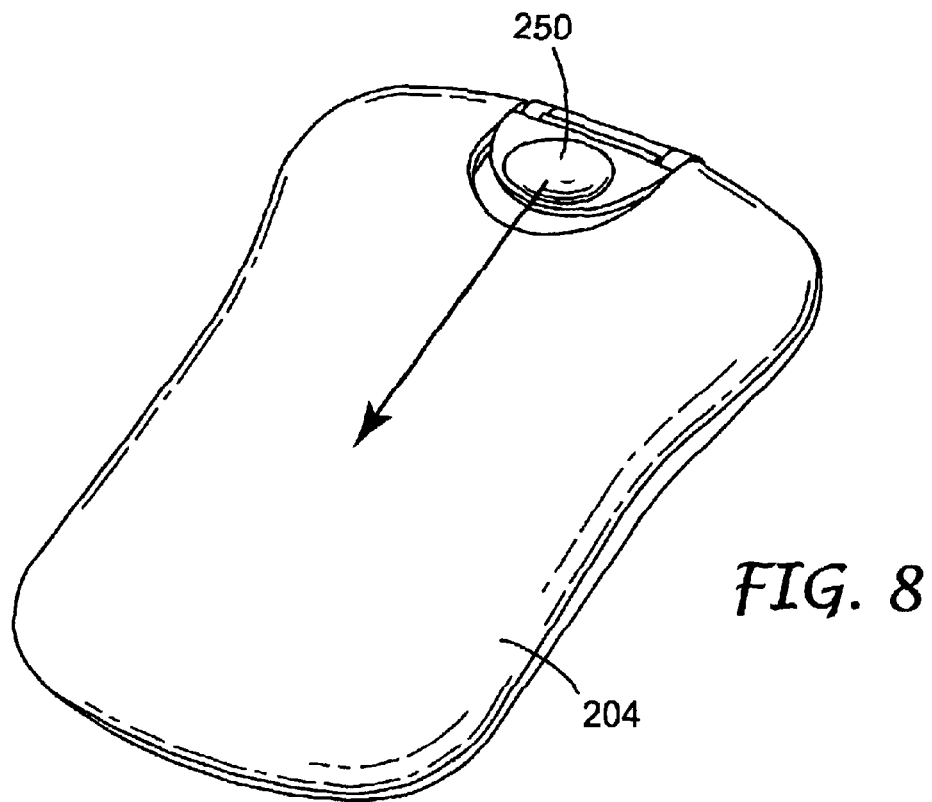
FIG. 8 is a perspective view of the underside of a housing with an underside button.
Figure 9:
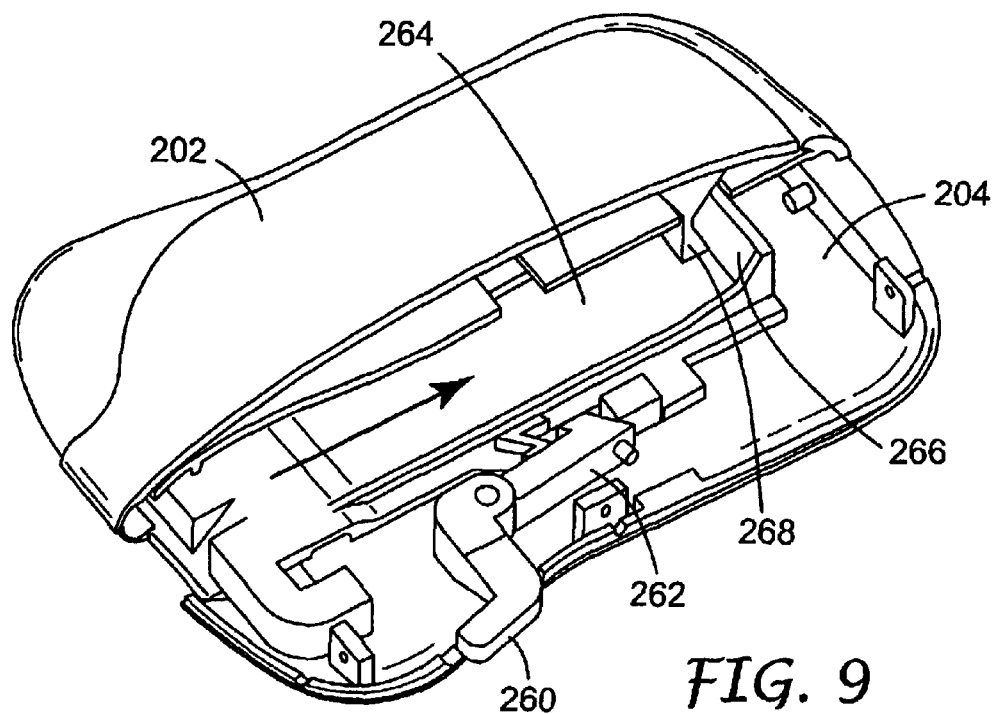
FIG. 9 is a perspective view showing a cutaway of a portion of the exterior cover, exposing some of the mechanisms used for opening and latching the cover.

In FIG. 7 a side button 260 is shown which may be depressed, pulled or otherwise engaged to open the exterior cover 202. In FIG. 8 an underside button 250 is shown which may be depressed, pulled or otherwise engaged to open the exterior cover 202. These buttons provide an opening mechanism that is not readily apparent to children and/or not readily engaged by children. The relation of the side button 260 to the opening mechanism of the exterior cover 202 is shown in FIG. 9. Activation of the side button 260 causes the side button latch 262 to disengage from or move in relation to the cover release member 264. The cover release member latch 266 is preferably integrally connected to the cover release member 264 such that movement of the cover release member 264 causes the cover release member latch 266 to disengage from the exterior cover hook 268, thus allowing the exterior cover 202 to open.

In a preferred embodiment, these buttons will only activate opening of the exterior cover when a "gravity switch" is engaged by positioning the dispenser in a particular, fixed orientation, such as parallel to the ground. Placing the dispenser in the proper alignment with relation to the ground, such that the gravity switch allows the dispenser to open, can be described as "engaging" the gravity switch. Preferably, the gravity switch is engaged when the underside of the dispenser is placed parallel to the ground.

Figure 10:
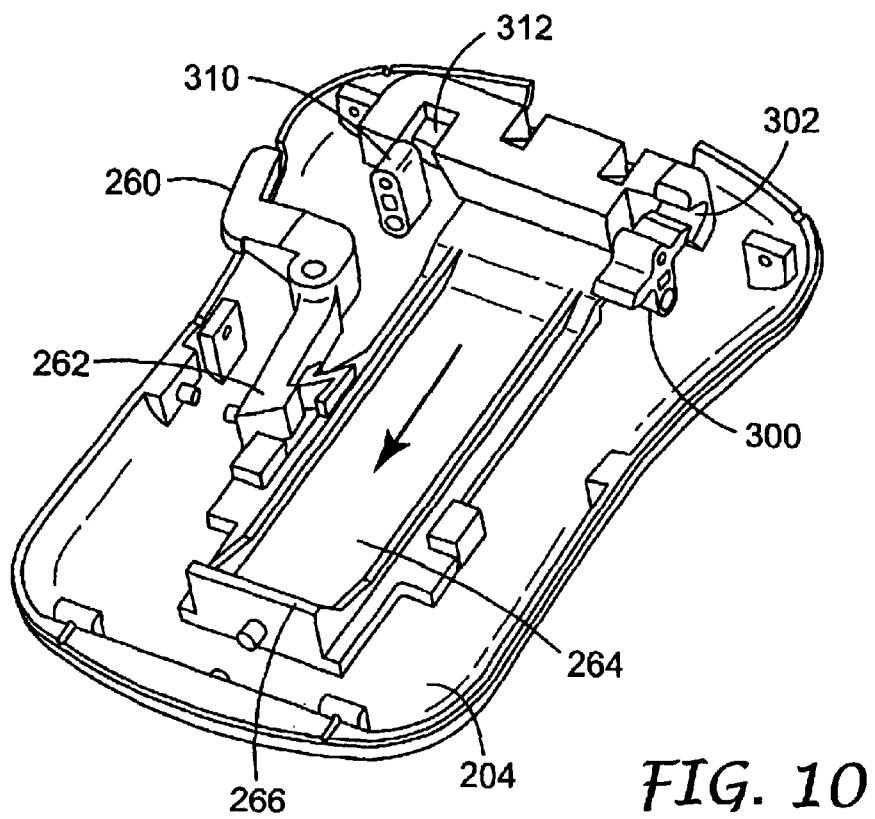
FIG. 10 is a perspective view of the interior of a housing showing mechanisms related to opening and latching of the exterior cover.

A preferred embodiment of a gravity switch mechanism is shown in FIG. 10, where the longitudinal gravity switch rocker 300 and transverse gravity switch rocker 310 are positioned relative to the cover release member 264 such that they do not interfere with the motion of the cover release member 264 that allows for opening of the exterior cover 202.

Figure 11:
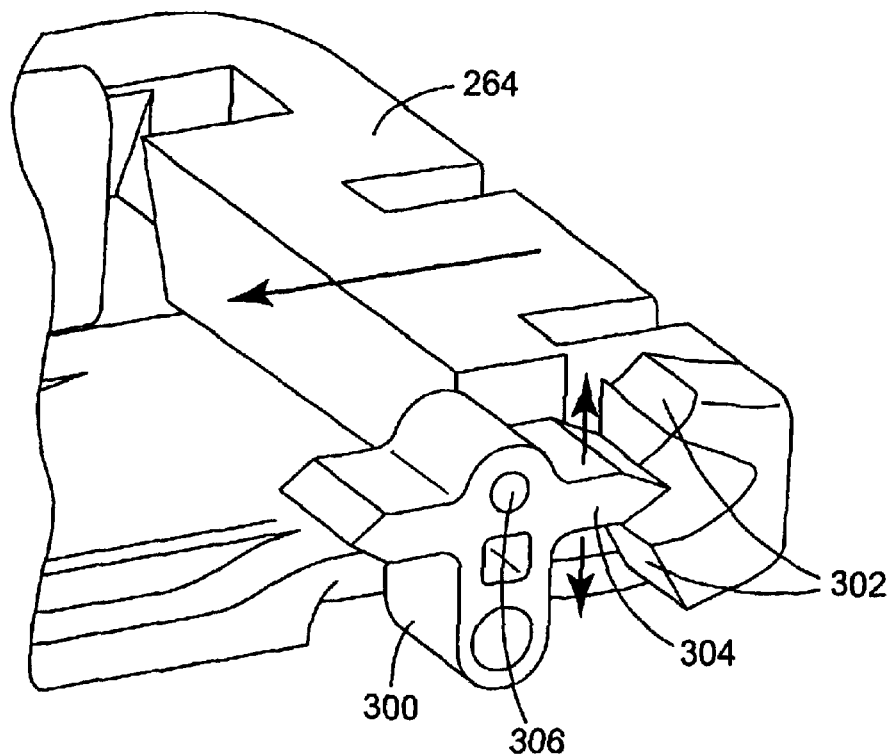
FIG. 11 is an exploded view of part A of a gravity switch.

As shown in FIG. 11, the longitudinal gravity switch rocker 300 is placed in relation to longitudinal gravity switch slot 302 so that when dispenser is held parallel to the ground the longitudinal gravity switch rocker 300 hangs in a neutral position from the longitudinal rocker pivot 306 and does not impede the motion of the cover release member 264, thereby allowing the dispenser to open when all other buttons or latch releases incorporated into the dispenser are engaged. Tilting of the dispenser of FIGS. 9 and 10 along the longitudinal axis will cause the rocker arm 304 to move in the direction of the arrows shown in FIG. 11. Tilting the dispenser beyond a minimum preset angle of tilt will cause the rocker arm 304 to engage the longitudinal gravity switch slot 302 sufficiently to prevent movement of the cover release member 264 and therefore prevent opening of the exterior cover 202. The preset angle may be adjusted based on the shape and size of both the rocker arm 304 and the longitudinal gravity switch slot 302. The minimum preset angle of tilt may be between 2° and 60°, more preferably between 10° and 30°, and most preferably about 20°.

Figure 12:
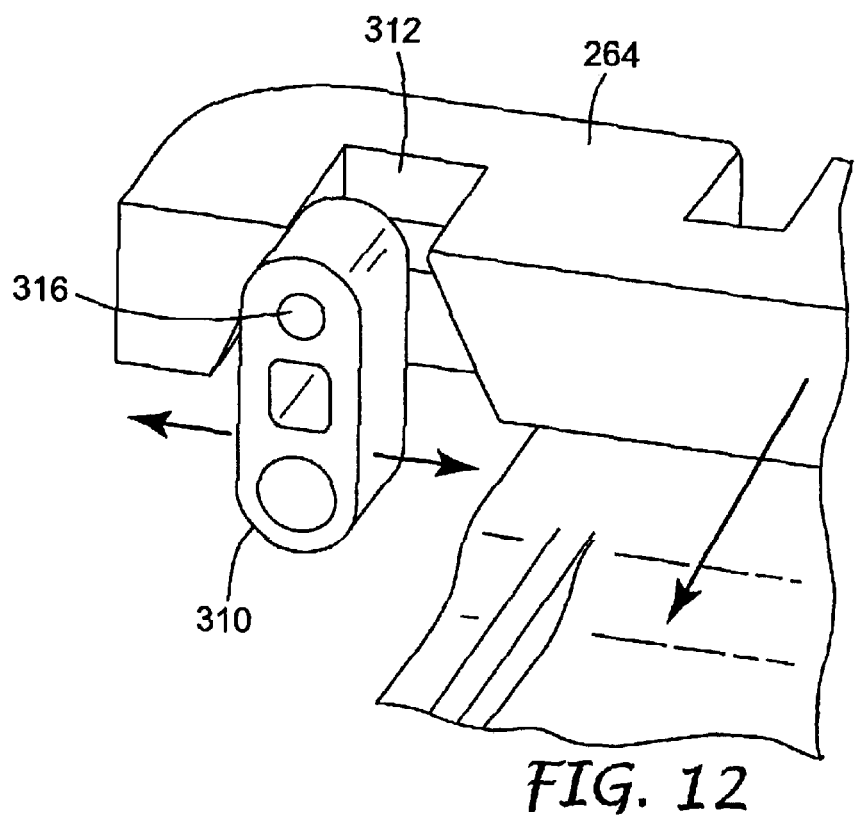
FIG. 12 is an exploded view of part B of a gravity switch.

As shown in FIG. 12, the transverse gravity switch rocker 310 is placed in relation to transverse gravity switch slot 312 so that when dispenser is held parallel to the ground the transverse gravity switch rocker 310 hangs in a neutral position from the transverse rocker pivot 316 and does not impede the motion of the cover release member 264, thereby allowing the dispenser to open when all other buttons or latch releases incorporated into the dispenser are engaged. Tilting of the dispenser of FIGS. 9 and 10 along the transverse axis will cause the transverse gravity switch rocker 310 to move in the direction of the arrows shown in FIG. 12. Tilting the dispenser beyond a minimum preset angle of tilt will cause the transverse gravity switch rocker 310 to engage the transverse gravity switch slot 312 sufficiently to prevent movement of the cover release member 264 and therefore prevent opening of the exterior cover 202. The preset angle may be adjusted based on the shape and size of both the transverse gravity switch rocker 310 and the transverse gravity switch slot 312. The minimum preset angle of tilt may be between 2° and 60°, more preferably between 10° and 30°, and most preferably about 20°.

The combination of the transverse and longitudinal gravity switches ensures that the exterior cover 202 cannot be opened unless the dispenser is placed substantially parallel to the ground as defined by the minimum preset angles of tilt for both the longitudinal and transverse directions. It should be understood that the gravity switches need not be aligned such that they are in the longitudinal and transverse directions in relation to the dispenser as a whole.

The underside button 250 in FIG. 8 is a preferred opening mechanism, since it is not visible to the patient when the dispenser is in the proper orientation to activate the gravity switch. This combination of underside button and gravity switch requires a user to place the dispenser in an orientation where the button is not directly visible when it is engaged. This activation of a hidden button can be particularly non-intuitive for a child and thus can be quite effective for preventing unauthorized or accidental opening of the dispenser by a child.

EXAMPLES

Example 1

As an example of the present invention, dispensers of the design generally shown in FIGS. 7 and 8 incorporating a gravity switch of the design generally shown in FIGS. 9 to 12 were molded out of polypropylene.

The dispensers were tested generally according to U.S. Code of Federal Regulations Title 16, Chapter 2, Section 1700.20, "Testing procedure for special packaging". This tests both the ability of children to gain access to the package contents and whether senior-adults are able to The child testing consists of two sequential five-minute testing periods during which time each child (aged 42 to 51 months) attempts to open the dispensers. The children are provided a closed dispenser and are given no instructions on how to open the dispensers, although they are told prior to the second testing period that they can use their teeth if they want to. This testing was performed with a subject group of 12 children. Results are reported as the total number of openings in each five-minute periods and a cumulative success rate, which is defined as the percentage of children who were unable to open the package during both test periods.

The senior-adult testing consists of a five-minute testing period followed by a one-minute testing period during which time each adult (aged 50 to 70) attempts to open the dispensers. The adults are provided with instructions for opening the dispensers and are allowed to refer to the instructions during each testing period. Adults who are unable to open the dispenser during the first five-minute test period are given two non-child-resistant packages to open during the subsequent one-minute test period. Those adults who are unable to open the non-child-resistant packages are not counted as part of the test panel results. This testing was performed with a subject group of 25 adults. Results are reported in Table 1 as the total number of packages opened in the first test period, the total packages opened in the second test period, and a cumulative success rate which is defined as the percentage of adults who were able to open the package during both test periods.

TABLE 1

| Test population | First Test Period (total openings) | Second Test Period (total openings) | Success rate |
| --- | --- | --- | --- |
| Child (n = 12) | 0 | 0 | 100% |
| Senior (n = 25) | 20 | 20 | 80% |

Example 2

As an example of the present invention inner cartridges with interior covers of the design generally shown in FIG. 5 were molded out of polyetherimide (Ultem™ supplied by GE Plastics).

The patches were prepared by combining 50% copolymer adhesive (67:13:20 isooctylacrylate:acrylamide:vinylacetate), 9% propylene glycol, 7% testosterone, and 34% terpineol, in a solvent mixture of ethyl acetate and methanol, where all percentages are by weight of solids. This composition was mixed on a drum roller until a homogeneous coating formulation was obtained. The formulation was coated at a wet thickness of 20 mil (508 μm) onto a fluoropolymer release liner. The coated release liner was dried in a 3-zone oven at temperatures ranging from 120° F. (49° C.) to 140° F. (60° C.). The coated liner was then laminated to a 2 mil (51 μm) polyester backing (Scotchpak™ 9732). The laminate was converted by die cutting into 45 cm² transdermal patches with a slit release liner. Stacks of patches were prepared by assembling thirty patches into an individual stack. The adhesive side of each patch in the stack was partially covered with a half-release liner (i.e., a release liner that covers half of the adhesive surface of the patch). The exposed adhesive portion of each patch was adhered to the patch below it, with the exception of the bottom patch in the stack which was adhered to a base liner that was affixed to the bottom of the inner cartridge. The patches were oriented so that the half-release liners were alternating from one side of the stack to the other. Each stack of patches was loaded into the bottom of an inner cartridge. The top of the inner cartridge was then ultrasonically welded to the bottom. The inner cartridge was sealed by heat sealing a foil seal over the aperture. A rubber gasket was placed around the sealed inner cartridge and an interior cover was closed against the inner cartridge and gasket.

Analysis of the initial drug and excipient content in the patches was performed by removing the foil seal from a cartridge and removing 10 patches for chromatographic analysis (patches no. 3, 6, 9, 12, 15, 18, 21, 24, 27, and 30 in order of removal). Drug and excipient content data was obtained using the following procedure. The liner was removed from the patches and the patches were placed in ajar where the backing and coating were extracted with a solution consisting of 75:25 by volume ethyl acetate (EtOH) :methanol (MeOH) with an internal standard of decanol. The samples were allowed to shake for two hours or until the adhesive was fully dissolved. Aliquots of the extraction solutions were then placed in autosampler vials for analysis. Analysis of the samples was performed by gas chromatography with flame ionization detection (GC-FID) using a J&W DB-1 capillary column (30 m×0.53 mm i.d., 1.5 µm film) with helium carrier gas.

The initial content was 7.1% testosterone, 6.1% propylene glycol, and 29.3% terpineol, on a weight basis of the coated formulation.

Samples of the sealed inner cartridges were placed at room temperature (25° C./60% RH) and accelerated temperature (40° C./75% RH) conditions for long term stability testing.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

We claim:

1. A transdermal/transmucosal patch dispenser, comprising:
    an inner cartridge defined by walls made of an impermeable material, wherein the inner cartridge is hermetically sealed during storage;
    a plurality of drug-containing transdermal/transmucosal patches contained within the inner cartridge;
    an aperture through which said transdermal/transmucosal patches may be withdrawn from the inner cartridge; and
    a housing comprising a base and an exterior cover, wherein the housing is adapted to fully enclose the inner cartridge and is capable of forming an impermeable seal defining an outer chamber.

2. The dispenser of claim 1, wherein the plurality of patches are arranged such that removal of one of the patches allows a next succeeding patch to be accessed for subsequent removal.

3. The dispenser of claim 2, wherein the patches are stacked on top of each other.

4. The dispenser of claim 3, wherein the patches are separably interconnected by a portion of adhesive adjacent alternating ends of the transdermal/transmucosal patches.

5. The dispenser of claim 3, wherein the patches are folded on top of each other and separably interconnected by a continuous release liner.

6. The dispenser of claim 5, wherein the base and the exterior cover are sized relative to the patches such that the exterior cover can be closed onto one patch so as to hold it in place while another patch extending out of the dispenser is separated.

7. The dispenser of claim 1, wherein the dispenser contains at least a one month supply of about thirty patches.

8. The dispenser of claim 1, wherein the patches contain at least one drug selected from the group consisting of estradiol, progestins, testosterone, and nitroglycerin.

9. The dispenser of claim 1, wherein the housing further comprises an interior cover.

10. The dispenser of claim 9, further comprising a gasket that is adapted to form a seal between the inner cartridge top and the interior cover.

11. The dispenser of claim 9, wherein the interior cover is integrally connected to the exterior cover.

12. A transdermal/transmucosal patch dispenser, comprising:
    an inner cartridge defined by walls made of an impermeable material;
    a plurality of drug-containing transdermal/transmucosal patches contained within the inner cartridge;
    an aperture through which said transdermal/transmucosal patches may be withdrawn from the inner cartridge; and
    an exterior cover adapted to enclose the aperture when the exterior cover is in a closed position,
    wherein the dispenser comprises a child-resistant mechanism.

13. The dispenser of claim 12, wherein the patches are arranged such that removal of one of the patches allows a next succeeding patch to be accessed for subsequent removal.

14. The dispenser of claim 13, wherein the patches are stacked on top of each other.

15. The dispenser of claim 14, wherein the patches are separably interconnected by a portion of adhesive adjacent alternating ends of the transdermal/transmucosal patches.

16. The dispenser of claim 14, wherein the patches are folded on top of each other and separably interconnected by a continuous release liner.

17. The dispenser of claim 12, wherein the dispenser contains at least a one month supply of about thirty patches.

18. The dispenser of claim 12, wherein the patches contain at least one drug that is a controlled substance.

19. The dispenser of claim 18, wherein the controlled substance is selected from the group consisting of morphine, fentanyl, buprenorphine, or testosterone.

20. The dispenser of claim 12, wherein the child-resistant mechanism comprises a gravity switch.

21. The dispenser of claim 12, wherein the dispenser comprises at least two child-resistant mechanisms.

22. The dispenser of claim 21, wherein one of the child-resistant mechanisms comprises a gravity switch.

23. A cartridge for use in a transdermal/transmucosal patch dispenser, comprising:
    an inner cartridge defined by walls made of an impermeable material, wherein the inner cartridge is hermetically sealed during storage;
    a plurality of drug-containing transdermal/transmucosal patches contained within the inner cartridge; and
    an aperture through which said transdermal/transmucosal patches may be withdrawn from the inner cartridge;
    wherein the cartridge is adapted to be enclosed by a housing comprising a base and an exterior cover, wherein the housing is capable of forming an impermeable seal defining an outer chamber.

24. A method of packaging transdermal/transmucosal drug-containing patches for convenient dispensing, comprising:
    providing a dispenser comprising an inner cartridge, an aperture, and
    a housing comprising a base and an exterior cover, wherein the housing is adapted to fully enclose the inner cartridge and is capable of forming an impermeable seal defining an outer chamber;
    packaging a plurality of transdermal/transmucosal drug-containing patches within said inner cartridge and arranging the patches so as to allow removal of one patch at a time in a predetermined sequential order through the aperture; and
    hermetically sealing the inner cartridge.

25. A method of packaging transdermal/transmucosal drug-containing patches for convenient dispensing, comprising:

providing a dispenser comprising an inner cartridge, an aperture, an exterior cover, wherein the exterior cover is adapted to fully enclose the aperture when the exterior cover is in a closed position, and a child-resistant mechanism;

packaging a plurality of transdermal/transmucosal drug-containing patches within said inner cartridge and arranging the patches so as to allow removal of one patch at a time in a predetermined sequential order through the aperture;

hermetically sealing the inner cartridge.

26. The method of claim 25 further comprising the step of closing the exterior cover so as to engage the child-resistant mechanism.

* * * * *

UNITED STATES PATENT AND TRADEMARK OFFICE
CERTIFICATE OF CORRECTION

PATENT NO. : 6,796,429 B2
DATED : September 28, 2004
INVENTOR(S) : Cameron, Brian D.

It is certified that error appears in the above-identified patent and that said Letters Patent is hereby corrected as shown below:

Title page,
Item [56], References Cited, FOREIGN PATENT DOCUMENTS, delete "6/1999" and insert -- 6/1998 --, therefor.

Column 3,
Line 61, after "et al." insert -- , Docket No. 52883US002 --.

Column 8,
Line 30, delete "adhesive         (67:13:20" and insert
-- adhesive (67:13:20 --, therefor.
Line 65, delete "ajar" and insert -- a jar --, therefor.

Signed and Sealed this

Fifteenth Day of February, 2005

JON W. DUDAS
*Director of the United States Patent and Trademark Office*